(12) United States Patent
Howard (10) Patent No.: US 8,479,479 B2
(45) Date of Patent: Jul. 9, 2013

(54) MEDICAL GLOVE PACKAGING

(71) Applicant: John C. Howard, South River, NJ (US)

(72) Inventor: John C. Howard, South River, NJ (US)

(73) Assignee: Liferose Products, Inc., South River, NJ (US)

( * ) Notice: Subject to any disclaimer, the term of this patent is extended or adjusted under 35 U.S.C. 154(b) by 0 days.

(21) Appl. No.: 13/683,678

(22) Filed: Nov. 21, 2012

(65) Prior Publication Data

US 2013/0081196 A1 Apr. 4, 2013

Related U.S. Application Data

(62) Division of application No. 13/588,424, filed on Aug. 17, 2012.

(60) Provisional application No. 61/537,442, filed on Sep. 21, 2011.

(51) Int. Cl.
*B65B 43/00* (2006.01)
*B67B 7/00* (2006.01)

(52) U.S. Cl.
USPC ............................................. 53/492; 53/461

(58) Field of Classification Search
USPC ............ 206/288, 300, 348, 438, 278; 53/429, 53/434, 116, 492, 461; 604/292; 2/16, 161.7, 2/168; 223/111
See application file for complete search history.

(56) References Cited

U.S. PATENT DOCUMENTS

| | | | |
|---|---|---|---|
| 3,037,621 A * | 6/1962 | Jackman | 206/294 |
| 3,366,228 A | 1/1968 | Nye | |
| 3,372,799 A | 3/1968 | Abildgaard | |
| 3,384,225 A * | 5/1968 | Nye | 206/278 |
| 3,391,855 A * | 7/1968 | Ansell | 229/72 |
| 3,637,411 A | 1/1972 | Agostinelli | |
| 3,870,150 A | 3/1975 | Hummel | |
| 3,892,314 A | 7/1975 | Semp | |
| 4,002,276 A | 1/1977 | Poncy et al. | |
| 4,068,757 A | 1/1978 | Casey | |
| 4,069,913 A | 1/1978 | Harrigan | |
| 4,099,614 A * | 7/1978 | Heissenberger | 206/299 |
| 4,143,109 A | 3/1979 | Stockum | |
| 4,153,054 A * | 5/1979 | Boone | 128/856 |
| 4,155,494 A * | 5/1979 | Poncy et al. | 223/111 |
| 4,159,069 A * | 6/1979 | Poncy et al. | 223/111 |
| 4,275,812 A | 6/1981 | Poncy et al. | |
| 4,668,224 A | 5/1987 | Lentz et al. | |
| 4,773,532 A | 9/1988 | Stephenson | |
| 4,845,780 A | 7/1989 | Reimers et al. | |

(Continued)

*Primary Examiner* — Luan K Bui
*Assistant Examiner* — Rafael Ortiz
(74) *Attorney, Agent, or Firm* — Watov & Kipnes, P.C.; Kenneth Watov (57) ABSTRACT

A packaging for a medical glove includes a cover defining an interior space, the cover further including a sealed end and an opposing end having an opening in communication with the interior space, at least one deployable member with a distal end extending from the cover opening into the interior space, and a proximal end secured to or being part of the cover opening, the at least one deployable member segregating the interior space into an inner clean and contaminant free area adjacent to the sealed cover end and an outer area adjacent to the cover opening, the distal end of the at least one deployable member being movable from a first position within the interior space to a second position outside the cover opening, and means for securely retaining the medical glove on the distal end of the at least one deployable member.

6 Claims, 10 Drawing Sheets

U.S. PATENT DOCUMENTS

| | | |
|---|---|---|
| 4,853,978 A | 8/1989 | Stockum |
| 4,876,747 A | 10/1989 | Coffey et al. |
| 4,884,300 A | 12/1989 | Vistins |
| 4,898,309 A | 2/1990 | Fischer |
| 4,915,226 A * | 4/1990 | Keenan .................. 206/438 |
| 4,951,815 A | 8/1990 | Ulbrich |
| 4,971,233 A * | 11/1990 | Keenan .................. 223/111 |
| 5,044,493 A | 9/1991 | Crawford et al. |
| 5,065,863 A * | 11/1991 | Moyet-Ortiz ............. 206/210 |
| 5,269,405 A | 12/1993 | Wood |
| 5,467,483 A | 11/1995 | Saadatmanesh et al. |
| 5,590,764 A | 1/1997 | Wood |
| 5,867,825 A * | 2/1999 | Scheerer .................... 2/69 |
| 6,016,570 A | 1/2000 | Vande Pol et al. |
| 6,112,936 A | 9/2000 | Arizmendi |
| 6,195,805 B1 | 3/2001 | Bourne et al. |
| 6,241,134 B1 | 6/2001 | Dunkel |
| 6,360,373 B1 | 3/2002 | Rehn et al. |
| 6,378,137 B1 | 4/2002 | Hassan et al. |
| 6,435,388 B1 | 8/2002 | Binder et al. |
| 6,539,549 B1 * | 4/2003 | Peters, Jr. ................ 2/16 |
| 6,730,380 B2 | 5/2004 | Littleton et al. |
| 6,805,963 B2 | 10/2004 | Janssen et al. |
| 6,925,874 B2 | 8/2005 | Puckett et al. |
| 6,972,148 B2 | 12/2005 | Janssen |
| 7,041,367 B2 | 5/2006 | Janssen et al. |
| 7,329,442 B2 | 2/2008 | Modha et al. |
| 7,624,455 B1 | 12/2009 | Bhalla |
| 2005/0000975 A1 | 1/2005 | Carco et al. |
| 2005/0006264 A1* | 1/2005 | Low ........................ 206/438 |
| 2005/0031817 A1 | 2/2005 | Littleton et al. |
| 2005/0186258 A1 | 8/2005 | Wang et al. |
| 2007/0170213 A1* | 7/2007 | Gaines et al. ............. 223/111 |
| 2009/0055994 A1 | 3/2009 | Waldbauer, Jr. |
| 2011/0083244 A1 | 4/2011 | Gellerstedt |
| 2011/0108587 A1* | 5/2011 | Williams ................. 223/111 |
| 2011/0191935 A1 | 8/2011 | Schneider |

* cited by examiner

MEDICAL GLOVE PACKAGING

PRIORITY CLAIM

The present Application claims the benefit of priority from U.S. Provisional Patent Application Ser. No. 61/537,442, filed on Sep. 21, 2011, the entire content of which is incorporated herein by reference. Also, the present Application is a Divisional from application Ser. No. 13/588,424 filed on Aug. 17, 2012 for "Medical Glove Packaging."

FIELD OF THE INVENTION

The present invention relates to medical and healthcare devices, and more particularly to a packaging for a medical glove configured to substantially minimize or eliminate inadvertent contamination of the medical glove especially during donning of the packaged medical glove.

BACKGROUND OF THE INVENTION

Healthcare acquired infections (HAI) are infectious diseases contracted by patients confined in a hospital or other healthcare facility, and acquire a disease that is not associated with their original medical problem. These infectious diseases are caused by microbes such as fungi, bacteria, viruses, parasites, spore forms thereof, and the like. Approximately two million people each year become sick in healthcare facilities from HAI. It is also among the top five leading causes of death in the United States (US). Such infections strike an average of 4.5 out of every 100 patients admitted to hospitals, and result in an average of 22 additional days of hospitalization. Total costs from HAI are estimated at between US$35 to US$88 billion annually, thus representing an increasing financial burden and declining healthcare quality in the US.

Proper hand hygiene and use of hospital or medical gloves have prevented even higher incidences of HAI. Such measures, particularly medical gloves, have helped prevent contamination between caregivers and patients. They provide a physical barrier for contact between the caregiver and the patient. However, it is estimated that only 50% of healthcare professionals adhere to proper hand hygiene and medical glove use. Often, the physical barrier provided by the medical gloves is compromised when the exterior of the medical gloves (i.e., side that contacts the patient) becomes contaminated. Such contamination can occur during donning of the medical gloves, retrieval of the medical gloves from their packaging, or even while in the packaging. Unfortunately, such improper attention to hand hygiene and medical glove use has become the most common mode of transmission of infectious diseases to patients.

Accordingly, there is a need in the art to develop a packaging for medical gloves designed to provide innovative layers of protection for minimizing or eliminating risks of contamination of the medical gloves during donning. There is a need to develop a packaging for medical gloves that provides enhanced protection for patients from HAI in a practical, efficient and cost effective manner. There is a need to develop a packaging for medical gloves that enables the user to don the medical gloves on both hands without outside assistance.

SUMMARY OF THE INVENTION

The present invention relates generally to a packaging for a medical glove and methods of making and using the same. The packaging of the present invention is specifically designed to prevent contamination of the exterior portion of the medical glove during donning of the packaged medical glove. In this manner, the risk of passing any potential contaminants to a subject or patient is at least substantially minimized or eliminated.

The packaging of the present invention is further designed to permit a user to don the medical glove without outside assistance. The packaging of the present invention can be used in any environment or setting where contamination by undesirable or potentially dangerous agents must be avoided, especially in hospital or healthcare settings. In the hospital or healthcare setting, the use of the packaging of the present invention will save numbers of lives and substantially reduce costs associated with healthcare acquired infections (HAI). The packaging of the present invention is relatively simple and cost effective to make and implement.

The packaging of the present invention generally includes a cover defining an interior space, where the cover further includes a sealed end and an opposing end having an opening in communication with the interior space, and at least one deployable member with a distal end extending from the cover opening into the interior space, and a proximal end secured to or being part of the cover opening, the at least one deployable member segregating the interior space into an inner clean and contaminant free area adjacent to the sealed cover end and an outer area adjacent to the cover opening. The distal end of the at least one deployable member is movable from a first position within the interior space to a second position outside the cover opening. The packaging further includes means for securely retaining the medical glove on the distal end of the at least one deployable member, wherein an exterior portion of the medical glove is disposed within the inner clean and contaminant free area in isolation from the outer area.

In one aspect of the present invention, there is provided a packaging for a medical glove, which includes:

a cover defining an interior space, the cover further including a sealed end and an opposing end having an opening in communication with the interior space;

at least one deployable member with a distal end extending from the cover opening into the interior space, and a proximal end secured to or being part of the cover opening, the at least one deployable member segregating the interior space into an inner clean and contaminant free area adjacent to the sealed cover end and an outer area adjacent to the cover opening;

the distal end of the at least one deployable member being movable from a first position within the interior space to a second position outside the cover opening; and means for securely retaining the medical glove on the distal end of the at least one deployable member, wherein an exterior portion of the medical glove is disposed within the inner clean and contaminant free area in isolation from the outer area.

In a further aspect of the present invention, there is provided a packaging for a medical glove, which includes:

a cover includes first and second opposed layers, the first and second layers defining an interior space;

the cover further including a sealed end and an opposing end having an opening in communication with the interior space;

a first panel with a distal end extending from the first layer at the cover opening into the interior space, and a proximal end secured to or being part of the cover opening, the distal end of the first panel being movable from a first position within the interior space to a second position outside the cover opening;

a second panel with a distal end extending from the second layer at the cover opening into the interior space, and a proximal end secured to or being part of the cover opening, the distal end of the second panel being movable from a first position within the interior space to a second position outside the cover opening;

the first and second panels, in combination, segregating the interior space into an inner clean and contaminant free area adjacent to the sealed cover end and an outer area adjacent to the cover opening; and means for securely retaining the medical glove on the distal ends of the first and second panels, wherein an exterior portion of the medical glove is disposed within the inner clean and contaminant free area in isolation from the outer area.

In another aspect of the present invention, there is provided a method for donning a medical glove, which includes the steps of:

(a) acquiring a medical glove contained in a packaging comprising:

a cover defining an interior space, the cover further including a sealed end and an opposing end having an opening in communication with the interior space;

at least one deployable member with a distal end extending from the cover opening into the interior space, and a proximal end secured to or being part of the cover opening, the at least one deployable member segregating the interior space into an inner clean and contaminant free area adjacent to the sealed cover end and an outer area adjacent to the cover opening;

the distal end of the at least one deployable member being movable from a first position within the interior space to a second position outside the cover opening; and means for securely retaining the medical glove on the distal end of the at least one deployable member, wherein an exterior portion of the medical glove is disposed within the inner clean and contaminant free area in isolation from the outer area.

(b) inserting user's hand into the outer area through the cover opening;

(c) placing the hand into the medical glove until the hand is fully seated therein; and (d) withdrawing the gloved hand from the clean area as the at least one deployable member is pulled out through the cover opening with the gloved hand.

BRIEF DESCRIPTION OF THE DRAWINGS

The following drawings are illustrative of embodiments of the invention and are not intended to limit the invention as encompassed by the claims forming part of the invention.

DETAILED DESCRIPTION OF THE INVENTION

The present invention is directed to a packaging for a medical glove and methods of making and using the same. The packaging of the present invention is specifically designed to prevent contamination of the exterior portion of the medical glove during donning of the packaged medical glove. Thus the present packaging facilitates donning of the medical glove without touching and contaminating the outside of the medical glove. In this manner, the risk of passing any potential contaminants to a subject or patient is at least substantially minimized or eliminated.

The packaging of the present invention is further designed to permit a user to don the medical glove without outside assistance. The packaging of the present invention can be used in any environment or setting where contamination by undesirable or potentially dangerous agents must be avoided, especially in hospital or healthcare settings. In the hospital or healthcare setting, the use of the packaging of the present invention will save numbers of lives and substantially reduce costs associated with healthcare acquired infections (HAI). The packaging of the present invention is relatively simple and cost effective to make and implement.

The packaging of the present invention generally includes a cover defining an interior space, where the cover further includes a sealed end and an opposing end having an opening in communication with the interior space, and at least one deployable member with a distal end extending from the cover opening into the interior space, and a proximal end secured to or being part of the cover opening, the at least one deployable member segregating the interior space into an inner clean and contaminant free area adjacent to the sealed cover end and an outer area adjacent to the cover opening. The distal end of the at least one deployable member is movable from a first position within the interior space to a second position outside the cover opening. The packaging further includes means for securely retaining the medical glove on the distal end of the at least one deployable member, wherein an exterior portion of the medical glove is disposed within the inner clean and contaminant free area in isolation from the outer area.

The term "medical glove" is intended to refer to a glove used during medical examinations, surgeries and procedures that help prevent contamination between caregivers (e.g., professional healthcare provider, nurses, doctors, and aides) and patients. The medical glove is typically disposable and made of different polymers including, but not limited to, latex, nitrile rubber, vinyl, polyethylene, polypropylene, neoprene and the like. Medical gloves may be powdered with a lubricant (e.g., cornstarch, talc) or unpowdered.

The present packaging for a medical glove is designed to eliminate or substantially minimize the probability of contamination of an exterior portion of the medical glove during its donning and subsequent removal therefrom. By maintaining the exterior portion of the medical glove in a clean, uncontaminated state, the risks of passing contaminants from caretaker to patient is greatly reduced or eliminated.

Figure 1:
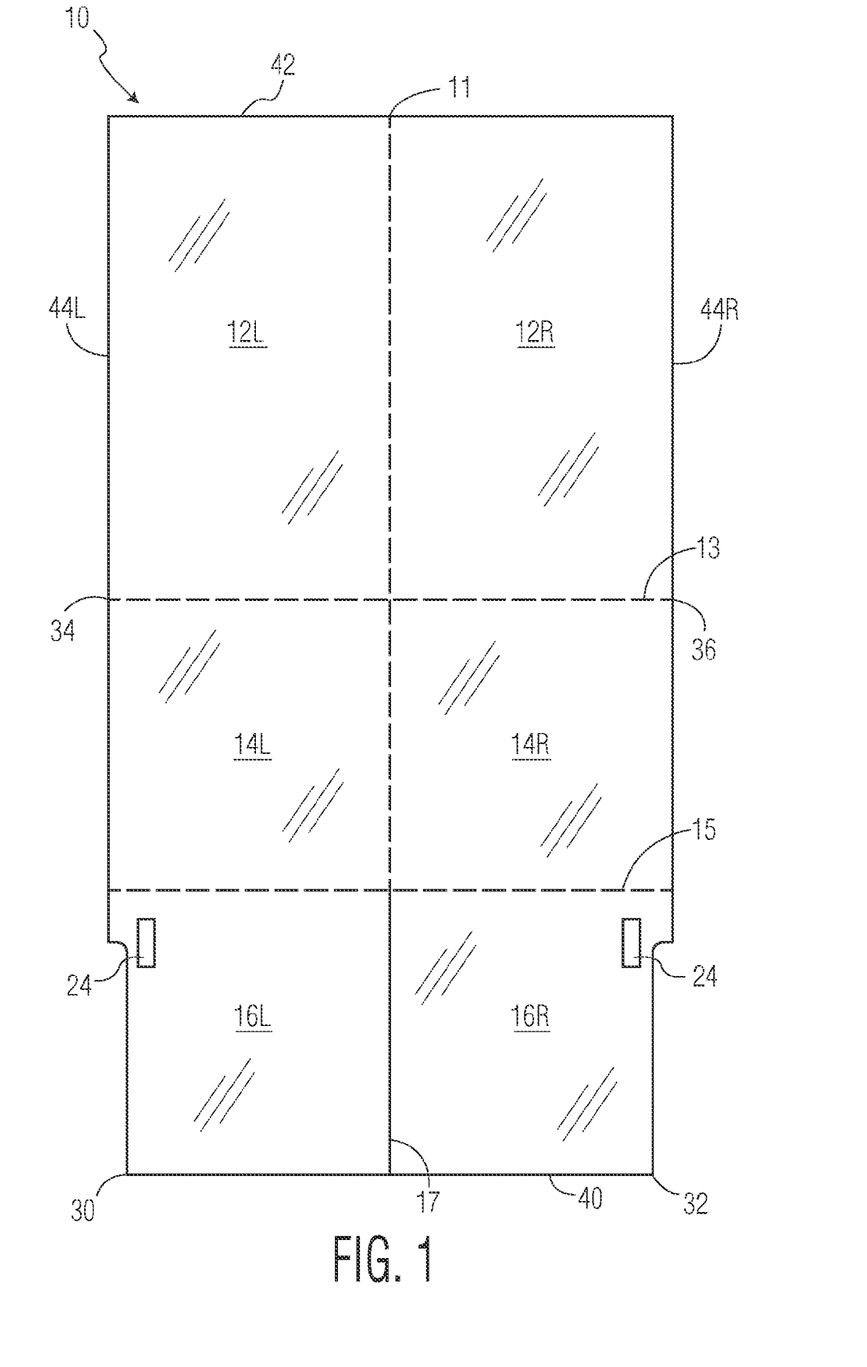
FIG. 1 is a top plan view of a packaging blank for constructing a packaging of a medical glove for one embodiment of the present invention.

With reference to FIG. 1, there is shown a packaging blank or sheet, identified generally by reference numeral 10, configured for constructing a medical glove packaging 50 (see FIGS. 4 through 11) in accordance with one embodiment of the present invention. Although the present invention is described in context of packaging a medical glove, it will understood that the present packaging is suitable for packaging any type or form of glove where it is desirable to maintain the exterior of the packaged glove in a clean, uncontaminated state relative to the ambient environment such as in a research laboratory setting, a clean room setting, in a manufacturing setting (e.g., semiconductor devices), or the like, especially during donning of the glove by the user. Thus, the term "glove" is intended to encompass any garment or article fitted for covering a user's hand, including, but not limited to, aeronautic gloves, medical gloves, food service gloves, laboratory gloves, and the like.

The packaging blank 10 is composed of any sheet material suitable for providing a physical barrier against passage of contaminants. The sheet material can be selected from optically transmissive materials including transparent and translucent materials. Preferably, the sheet material can be selected from polymers, papers, metals, or combinations thereof. More preferably, the sheet material is a polymer including, but not limited to, polypropylene, polyethylene, polyacrylonitrile, polystyrene, polyurethane, rayon, cellulose, celluloid, rayon, delrin, resins, rubber, nylon, and the like. In a preferred embodiment of the present invention, the sheet material is selected from polypropylene.

The packaging sheet 10 includes a pair of upper sections 12L and 12R, a pair of lower sections 14L and 14R, a pair of panels 16L and 16R, a bottom end or edge portion 40, a top end or edge portion 42, side edge portions 44L and 44R. The upper sections 12L and 12R of the sheet 10 are formed by fold line 11 and panel alignment line 13. The lower sections 14L and 14R of the sheet 10 are formed by the fold line 11, the panel alignment line 13 and fold line 15. The panels 16L and 16R are formed by the fold line 15 and separated from one another along score or cut line 17.

Optionally, a pair of single-sided adhesive reinforcing strips 24 are placed at the base portion of the panels 16L and 16R proximate the fold line 15 to minimize any tearing or weakness at those points. The strips 24 can be selected from suitable products such as SCOTCH® MAGIC™ Greener Tape marketed by 3M of St. Paul, Minn.

The panels 16L and 16R include corners 30 and 32, respectively, at opposing sides thereof. The panel alignment line 13 defines where the distal end of the panels 16L and 16R, once folded along fold line 15, are aligned at the proper position as will be described hereinafter.

Figure 2:
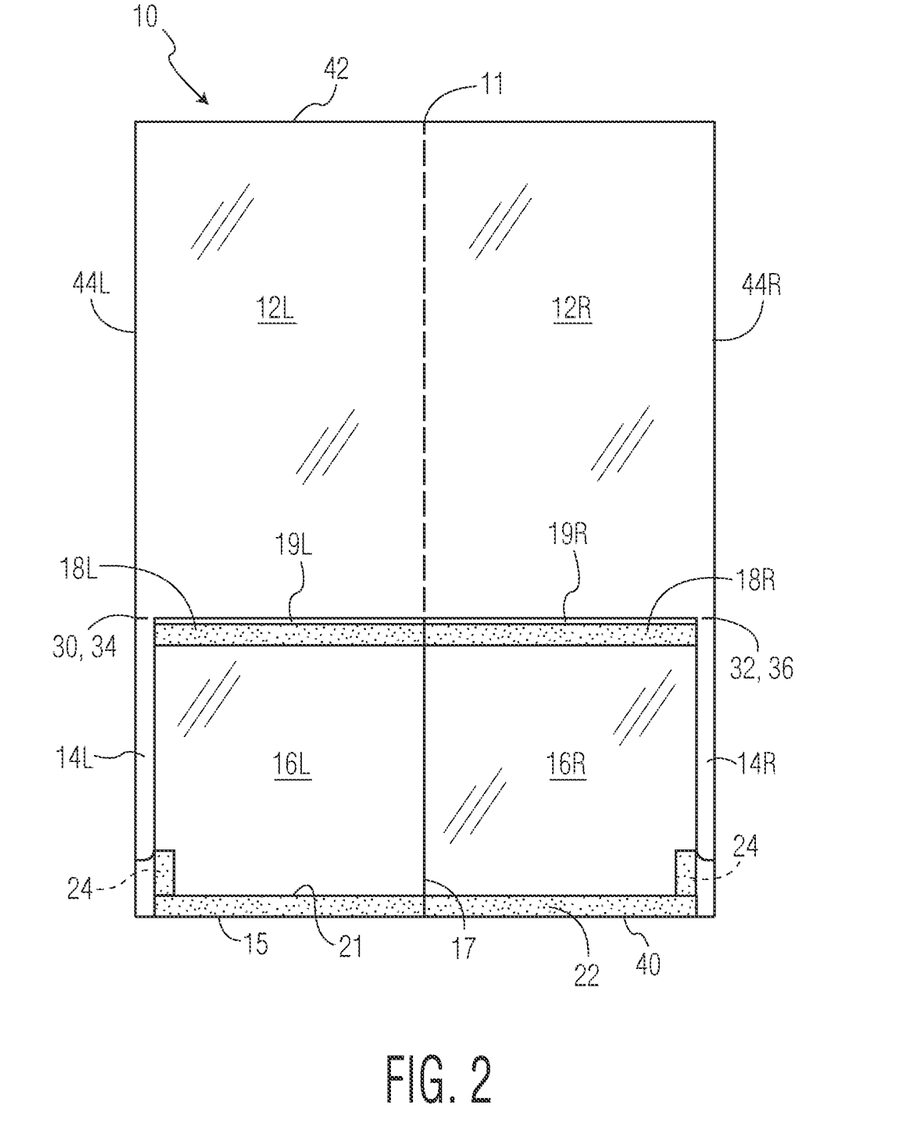
FIG. 2 is a top plan view of the packaging blank with adhesive strips in a partially folded configuration in accordance with the present invention.
Figure 3:
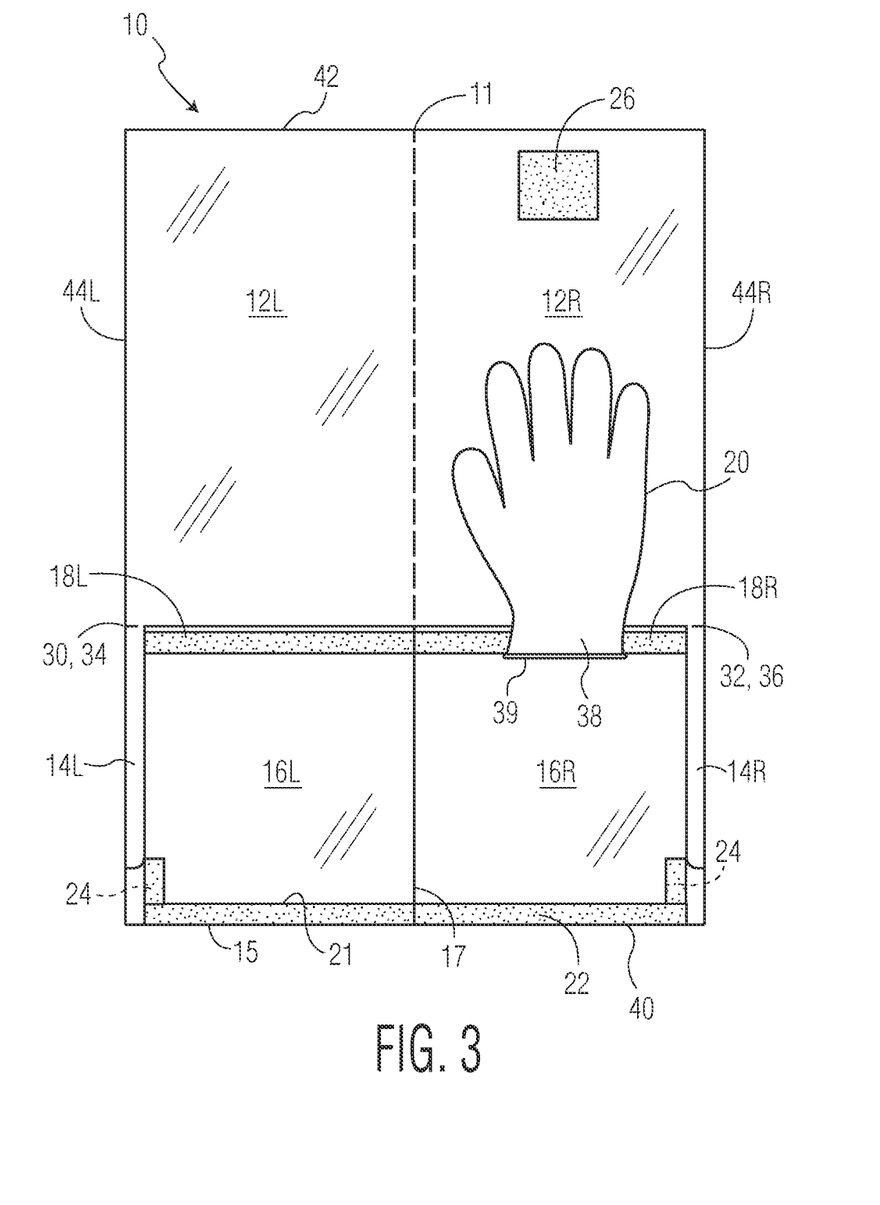
FIG. 3 is a top plan view of the packaging blank with a medical glove positioned for packaging in accordance with the present invention.
Figure 4:
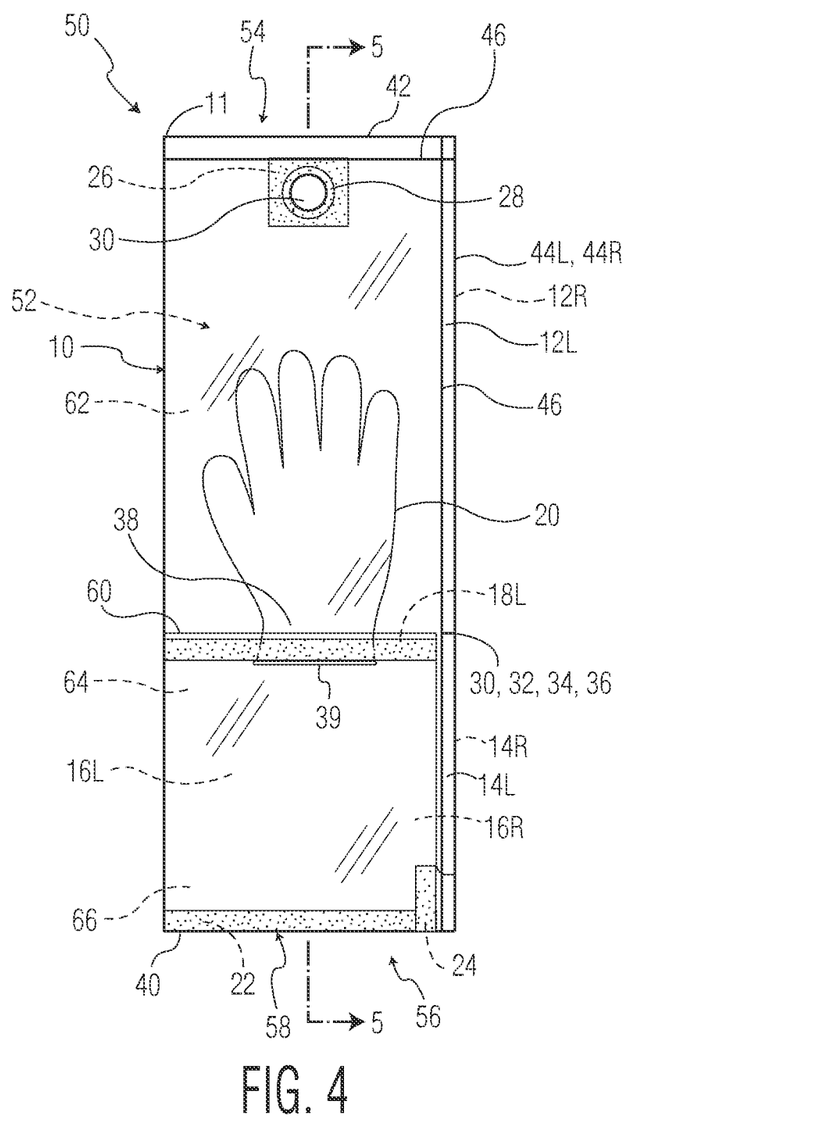
FIG. 4 is an elevational view of a packaging for a medical glove for one embodiment of the present invention.

Referring to FIGS. 2 through 4, the packaging sheet 10 is shown at different construction phases of the present packaging 50 for a medical glove for one embodiment of the present invention. Construction of the medical glove packaging 50 is initiated by folding the panels 16L and 16R onto the respective lower sections 14L and 14R of the sheet 10 aligning the panel corners 30 and 32 with corresponding points 34 and 36 located on the panel alignment line 13 (as shown in FIG. 2).

As shown in FIG. 2, once the panels 16L and 16R are folded onto the corresponding lower sections 14L and 14R as described above, double-sided adhesive strips 18L and 18R are applied along corresponding top distal edge portions 19L and 19R of the panels 16L and 16R. A double-sided adhesive strip 22 is applied along a top proximal edge portion 21 extending proximately along the fold line 15. Preferably, the adhesive strips 18L, 18R and 22 include an acrylic adhesive supported on a polyester film carrier. More preferably, the adhesive strips 18L, 18R and 22 include different degrees of tack on each side with the higher tack side applied to the sheet 10. The adhesive strips 18L and 18R and 22 can be selected from suitable products such as 3M™ Removable Repositionable Tape 9415PC marketed by 3M of St. Paul, Minn.

As shown in FIG. 3, a medical glove 20 is positioned on a top surface of the upper panel 12R with a lower portion 38 of the medical glove 20 placed securely in contact with the adhesive strip 18R for secure retainment thereon. The opening 39 of the medical glove 20 is positioned proximate to the panel 16R of the sheet 10. A double-sided adhesive patch 26 is affixed centrally on the top portion of the upper section 26 proximate top end 42 of the sheet 10. The upper and lower sections 12L and 14L and the panel 16L are folded along fold line 11 in an overlapping arrangement over corresponding upper and lower sections 12R and 14R and panel 16R (see FIG. 4).

As shown in FIG. 4, the adhesive strip 18L adhesively contacts and retains the lower portion 38 of the medical glove 20 on the side opposite from the adhesive strip 18R. The remaining portions of the adhesive strip 18L overlays the adhesive strip 18R for adhesively sealing and retaining engagement therebetween. The combination of the adhesive strips 18L and 18R securely positions the medical glove 20 in position within the folded sheet 10. The overlapping top edge portions 42 and side edge portions 44L and 44R are permanently sealed to one another via seal lines 46 which may be produced by any suitable sealing means such as, for example, heat sealing, induction sealing, adhesive sealing, ultrasonic sealing, friction sealing, laser sealing, and the like.

The overlapping adhesive strips 22 provide retaining engagement therebetween and seal the interior of the sheet 10 from the ambient. The portion of the sheet 10 through the center of the adhesive patch 26 to form an aperture 30 which is sealed off from the interior of the sheet 10 as will be further described hereinafter. The resulting medical glove packaging 50 is constructed to securely seal the medical glove 20 from the ambient and prevent entry of any outside contaminants (e.g., bacteria, viruses, spores, and parasites) during storage and transport.

Figure 5:
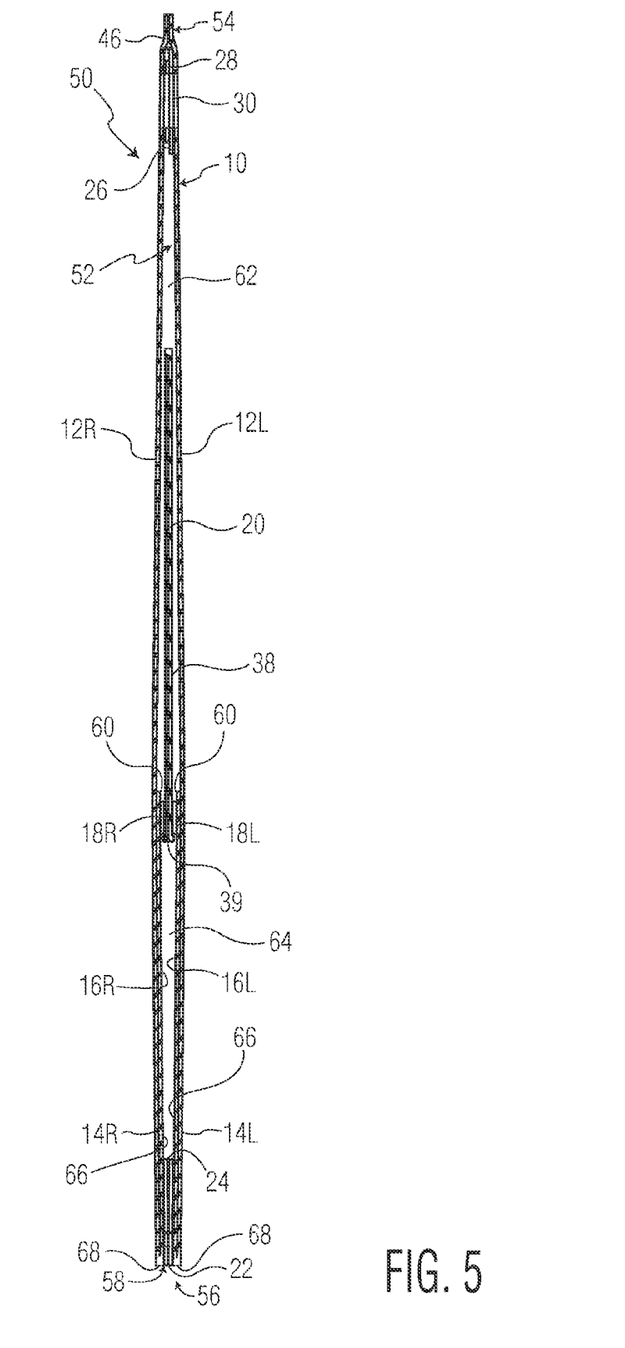
FIG. 5 is a cross sectional view of the packaging and medical glove taken along lines 5-5 of FIG. 4 in accordance with the present invention.

With reference to FIGS. 4 and 5, the medical glove packaging 50 includes the packaging sheet 10 defining an interior space 52, a sealed end 54, and an opposing end 56 having an opening 58 in communication with the interior space 52. The medical glove packaging 50 further includes the opposed panels 16L and 16R each having a distal end 60, which are deployable through the packaging opening 58 as will be described hereinafter. The adhesive strips 22 located on the proximal ends of the panels 16L and 16R, respectively, are adhesively engaged to one another to maintain the packaging opening 58 in a closed and sealed state from ambient environment during storage and transport.

The proximal ends 66 of the panels 16L and 16R are connected to the sheet 10 to form a hinge 68 (as shown best in FIG. 5). In the present embodiment, the panels 16L and 16R are in the form of flaps. The distal ends 60 of the opposed panels 16L and 16R are configured to move from a packaged position within the interior space 52 to an unpackaged position outside the cover opening 58 as will be further described hereinafter.

In the packaged position, the opposed panels 16L and 16R separates the interior space 52 into an inner clean and contaminant free area 62 located adjacent to the sealed end 54 and an outer area 64 located adjacent to the opening 58. The adhesive strips 18L and 18R, disposed at the respective distal ends 60 of the opposed panels 16L and 16R, securely retain the medical glove 20 in the inner clean and contaminant free area 62 of the space 52, while the opening 39 of the medical glove 20 is accessible through the outer area 64 of the space 52. During donning of the medical glove 20, the outer area 64 becomes contaminated by the presence of the user's hand.

The adhesive strips 18L and 18R seal the distal ends 60 of the panels 16L and 16R together to isolate the outer area 64 from the inner clean and contaminant free area 62 and to prevent passage of contaminants into the inner clean and contaminant free area 62. Preferably, the combination of adhesive strips 18L and 18R adhesively contact the medical glove 20 around its lower portion 38 proximate the glove opening 39.

The packaging 50 further includes a fastening component 28 (see FIGS. 5 and 6) defining an aperture 30 disposed on the sheet 10 for fastening to a fixed structure or workpiece (not shown). In a preferred embodiment of the present invention, the fastening component 28 is located proximate the sealed end 54 of the packaging 50. The fastening component 28 is formed by the inside surfaces of the upper sections 12L and 12R adhesively affixed to one another by adhesive patch 26, with the aperture 30 disposed therein to create a structure in the form of a ring. The fastening component 28 facilitates removal of the donned medical glove 20 from the packaging 50 as will be described hereinafter.

Figure 6:
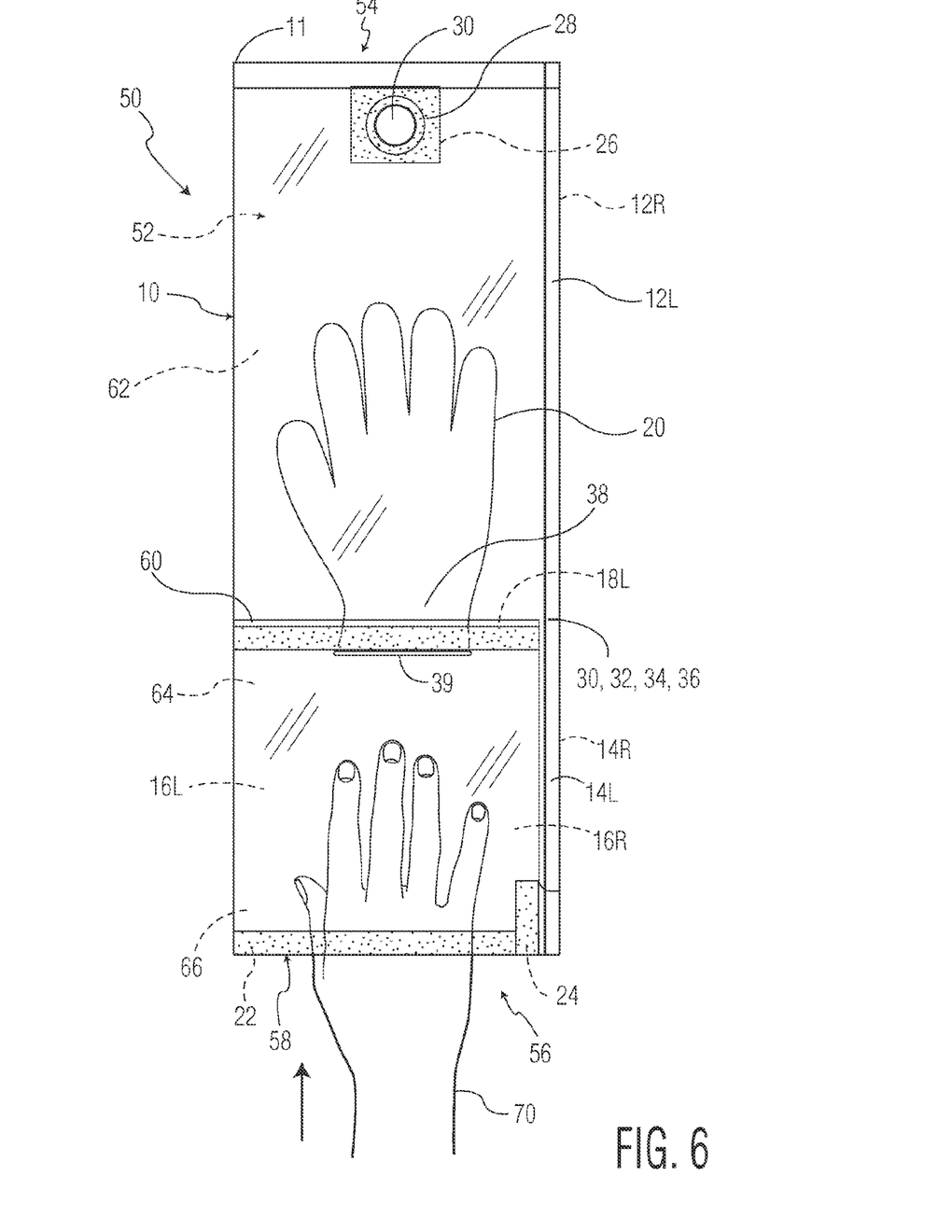
FIG. 6 is a top plan view of the packaging with a user's hand partially inserted therein for donning the medical glove in accordance with the present invention.
Figure 7:
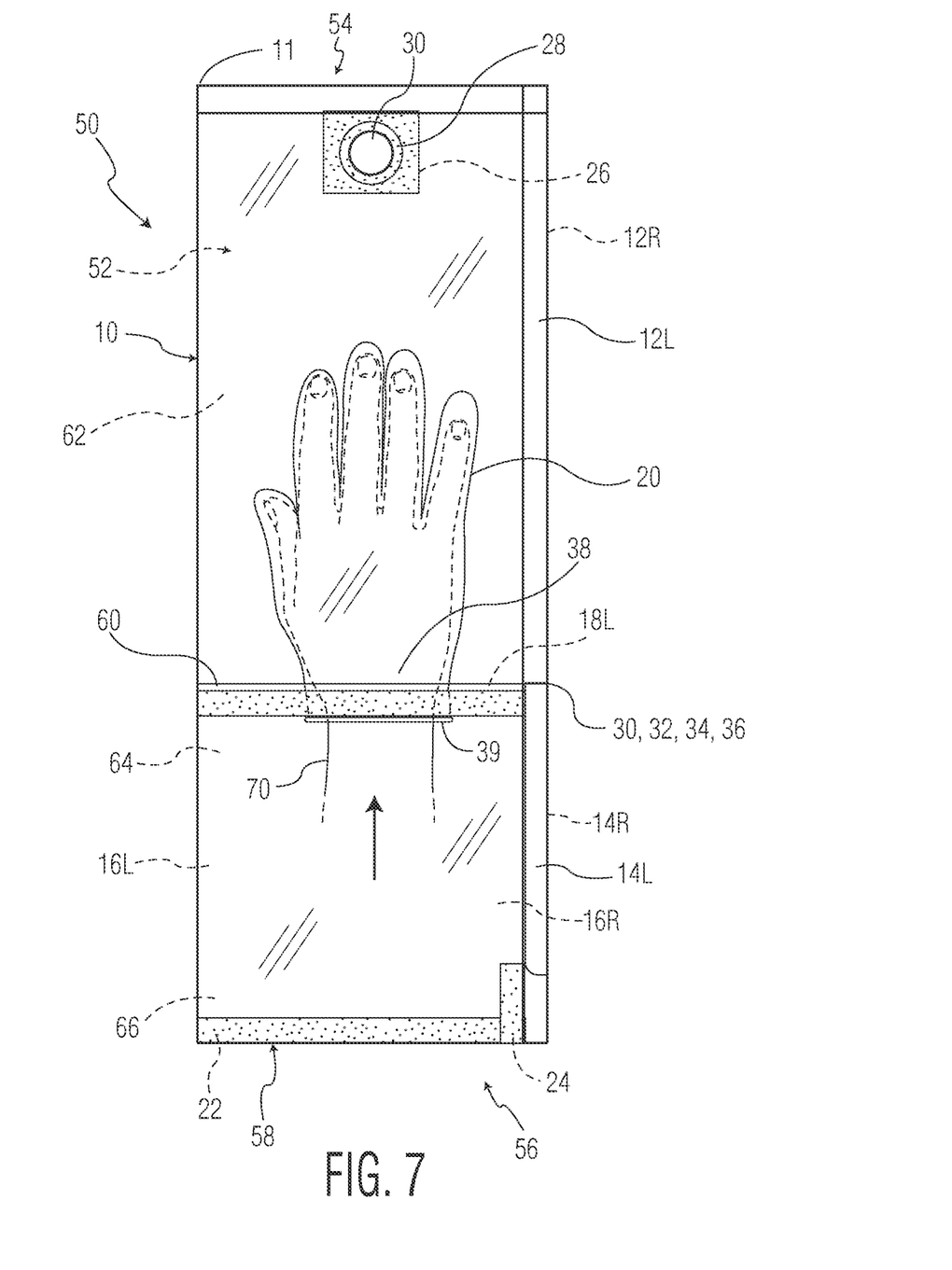
FIG. 7 is a top plan view of the packaging with the user's hand in the process of donning and within the medical glove in accordance with the present invention.

With reference to FIGS. 6 through 11, a process for donning a medical glove contained in the medical glove packaging 50 will be shown and described. As shown in FIG. 6, the opening 58 is pulled apart to separate the adhesive strips 22 to allow a user's hand 70 to be inserted into the outer area 64 between the panels 16L and 16R. As shown in FIG. 7, the user's hand is inserted into the medical glove 20 through the glove opening 39. The user can hold the wristband of the medical glove with his other hand through the sheet 10 until the user's hand is fully seated therein. During donning of the medical glove 20, the adhesive strips 18L and 18R remain intact to maintain the isolation of the exterior portion of the medical glove 20 within the inner clean and contaminant free area 62 from the outer area 64 (now contaminated by the user's hand).

Optionally, with the gloved hand 70 still in the package 50, the user can obtain a second medical glove packaging 50 to glove the user's other hand and follow the same steps as outlined above for the user's first hand 70. The user can use the gloved hand 70 while still in its packaging 50 through the sheet 10 to assist the donning of the glove 20 on the user's other hand.

Figures 8, 9:
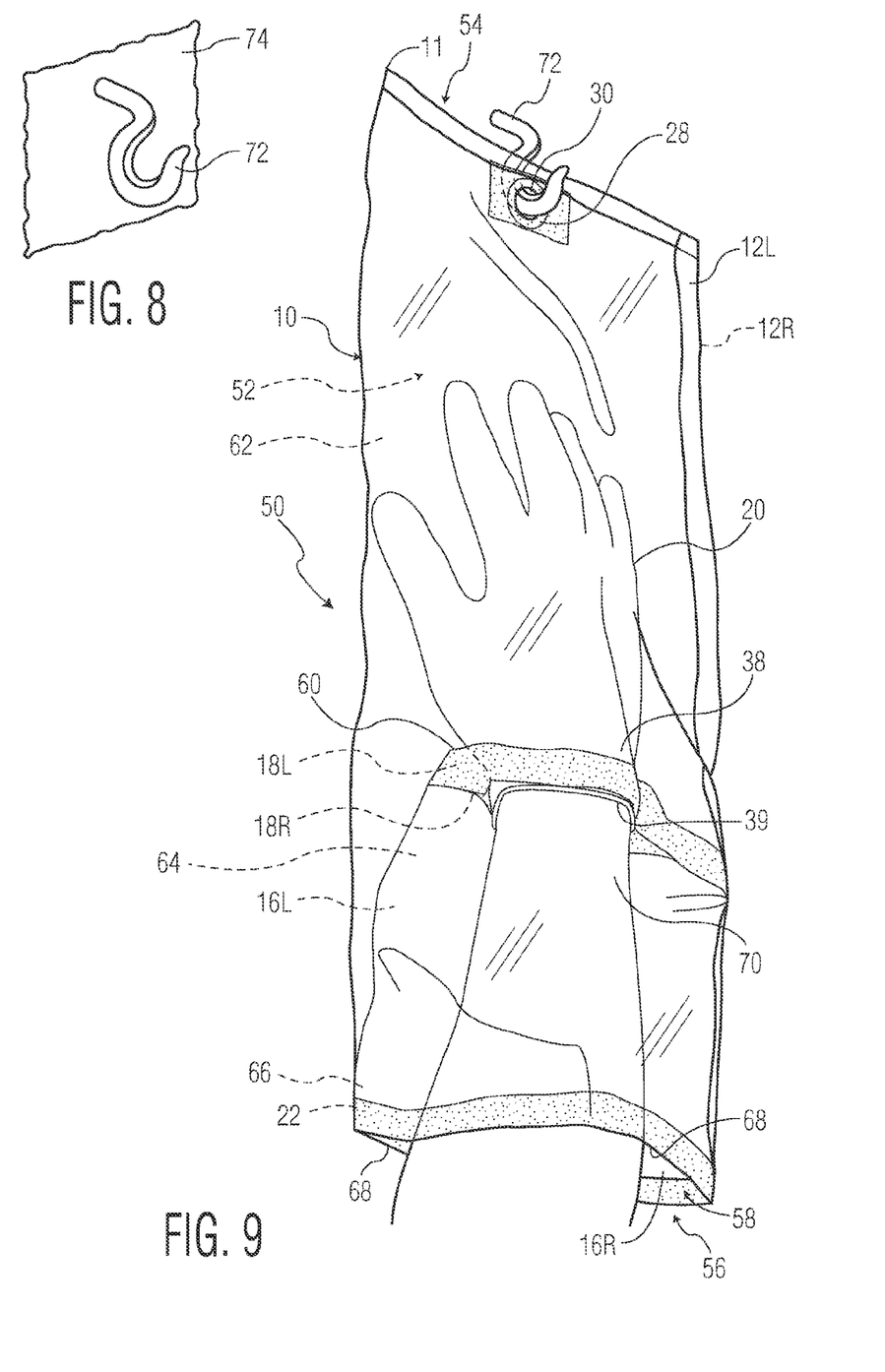
FIG. 8 is a perspective view of a hook mounted on a wall in accordance with the present invention.
FIG. 9 is a perspective view of the packaging fastened to the hook with the user's gloved hand therein in accordance with the present invention.

As shown in FIG. 9, the user's hand 70 is fully seated in the medical glove 20 within the inner clean and contaminant free area 62. In the next step, the user is ready to remove the gloved hand 70 from the packaging 50 with the exterior portion of the medical glove 20 maintained in a clean, uncontaminated state. The user affixes the packaging 50 to a hook 72 mounted on a fixed structure such as a wall 74 (see FIG. 8) via the fastening component 28. Once affixed, the user can withdraw the gloved hand 70 from the packaging 50. It will be understood that two hooks 72 positioned spaced apart from one another can be assembled to permit a user to remove both of the user's gloved hands from the corresponding packagings 50 at the same time.

Figure 10:
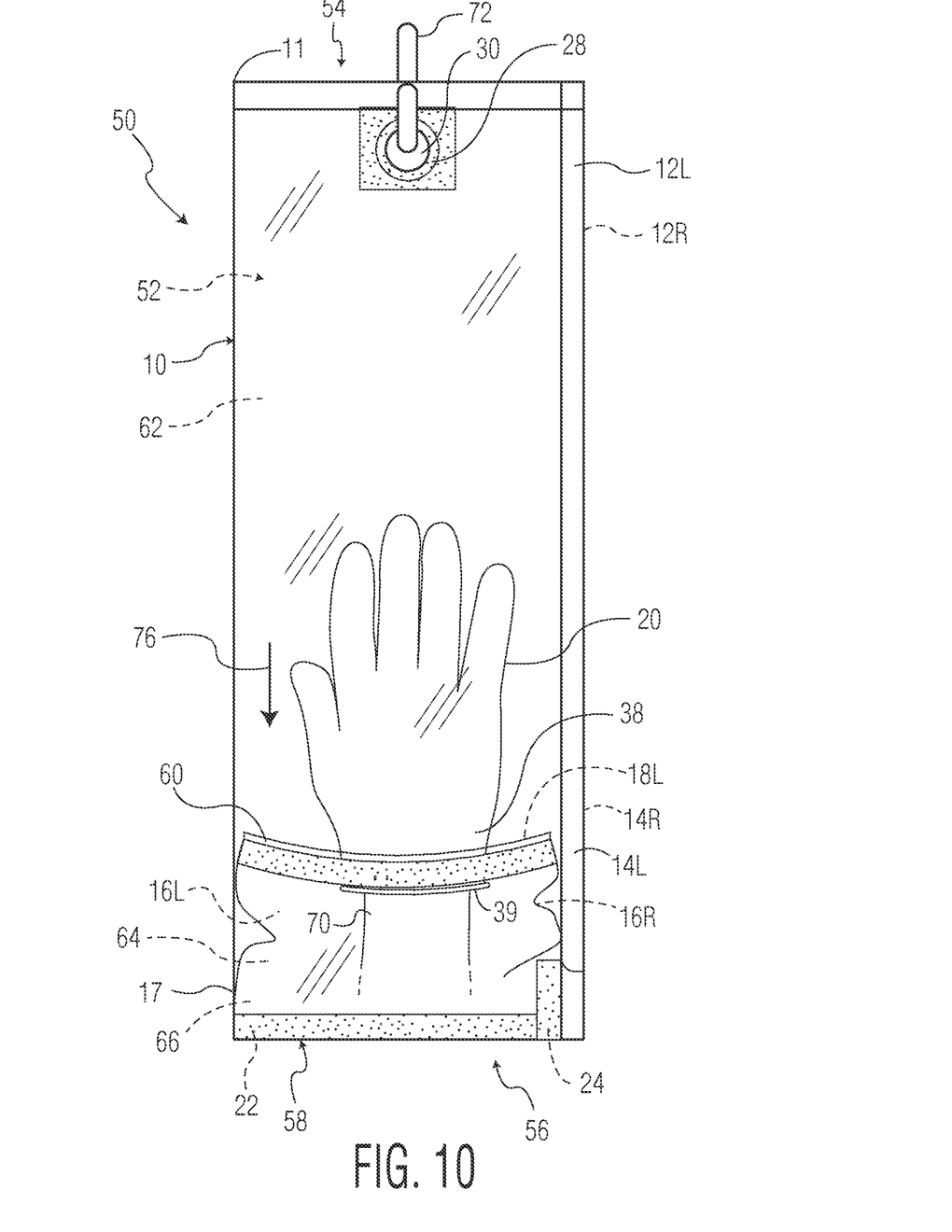
FIG. 10 is an elevational view of the packaging fastened to the hook as the user's gloved hand withdraws therefrom in accordance with the present invention.

As shown in FIG. 10, the gloved hand 70 begins to be withdrawn in the direction of arrow 76 within the packaging 50. As the distal ends 60 of the panels 16L and 16R firmly attached to the medical glove 20 move with the user's gloved hand 70 towards the packaging opening 58, the panels 16L and 16R move with the glove 20 keeping the exterior portion of the glove 20 isolated from the outer area 64. Thus, the panels 16L and 16R prevent contact between the contaminated surfaces of the outer area 64 and the exterior portion of the medical glove 20, as the gloved hand 70 is being withdrawn through the packaging opening 58.

Figure 11:
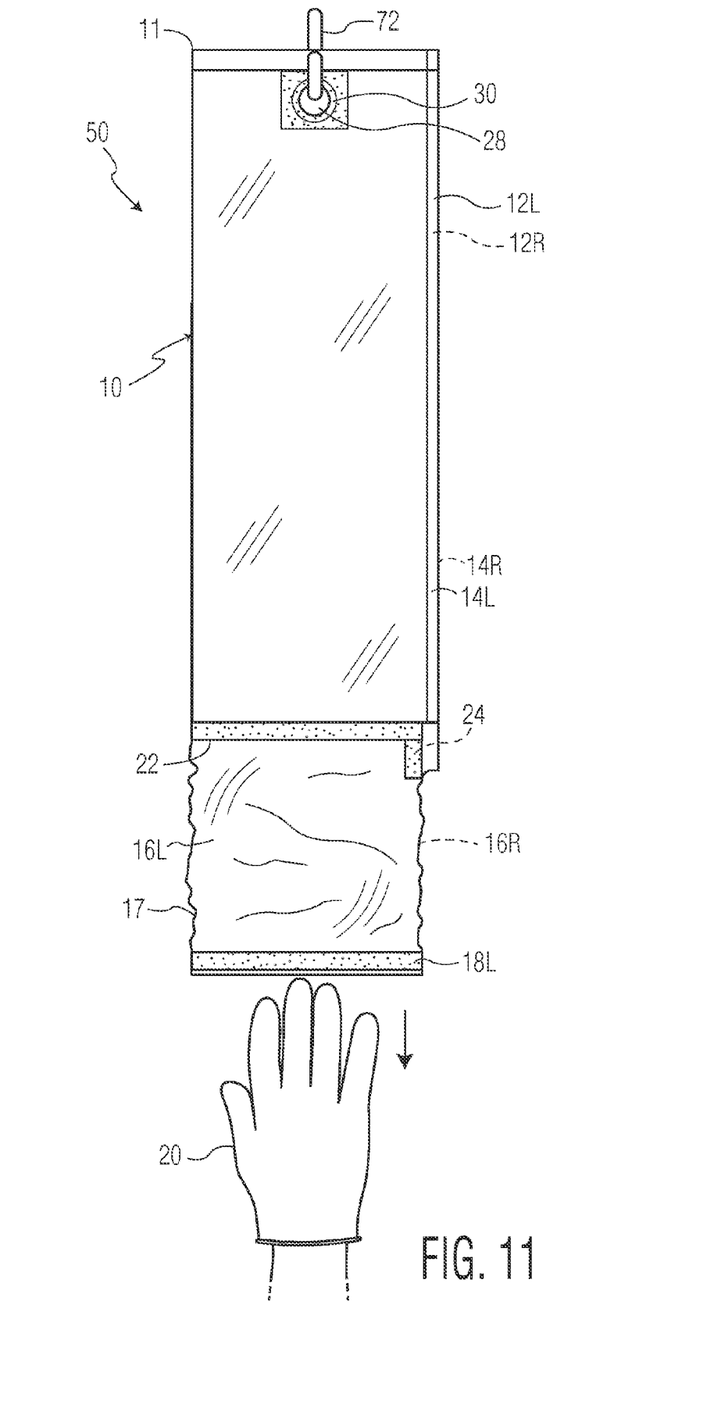
FIG. 11 is an elevational view of the packaging as the user's gloved hand is completely withdrawn therefrom in accordance with the present invention.

The clean, uncontaminated sides of the panels 16L and 16R of the inner clean and contaminant free area 62 remain in continuous contact with the medical glove 20 as the panels 16L and 16R flip out from the interior space 52 of the packaging 50. In this manner, the outer portion of the medical glove 20 is preserved in its clean, uncontaminated state as it is drawn through the packaging opening 58. The process is complete when the medical glove 20 is drawn out of the packaging 50 with the panels 16L and 16R fully deployed as shown in FIG. 11.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A method for donning a medical glove, comprising the steps of:
   (a) acquiring a medical glove contained in a packaging comprising:
      a cover defining an interior space, said cover further including a sealed end and an opposing end having an opening in communication with said interior space;
      at least one deployable member, excluding a medical glove, forming part of said cover, having a proximal end and a distal end extending from the cover opening into said interior space, and said proximal end being secured to the cover opening, said at least one deployable member segregating the interior space into an inner clean and contaminant free area adjacent to the sealed cover end and an outer area adjacent to the cover opening;
      said distal end of the at least one deployable member being pivotably movable from a first position within the interior space to a second position outside the cover opening; and
      means for securely retaining the medical glove on the distal end of said at least one deployable member, wherein an exterior portion of the medical glove is disposed within the inner clean and contaminant free area in isolation from the outer area;
   (b) inserting a user's hand into the outer area through the cover opening;
   (c) placing said hand into the medical glove until said hand is fully seated therein; and
   (d) withdrawing the gloved hand from the clean area as the at least one deployable member is pulled out through the cover opening with the gloved hand.

2. The method of claim 1, prior to step (d), further comprising:
   repeating steps (a) through (c) for the user's other hand with the user using the user's originally gloved hand while still within said cover to assist in seating the user's other hand in the corresponding medical glove contained in its packaging; and
   implementing step (d) for removing both gloved hands from their associated packaging.

3. The method of claim 1, wherein the packaging further comprises means located on said cover for fastening said cover to a fixed structure.

4. The method of claim 3, wherein the fastening means is disposed on the cover at an end opposite from the cover opening.

5. The method of claim 4, wherein the fastening means is a ring.

6. The method of claim 5, prior to the withdrawing step, further comprising the step of engaging a fixed hook through the ring to immobilize the cover of the packaging to permit easy withdrawal of user's gloved hand therefrom.

* * * * *